US00PP25034P3

(12) United States Plant Patent
Suphachadiwong

(10) Patent No.: US PP25,034 P3
(45) Date of Patent: Nov. 4, 2014

(54) ***PHALAENOPSIS* PLANT NAMED 'SUPHAL1305'**

(50) Latin Name: ***Phalaenopsis* hybrid**
Varietal Denomination: SUPHAL1305

(71) Applicant: Thumrong Suphachadiwong, Chonburi (TH)

(72) Inventor: Thumrong Suphachadiwong, Chonburi (TH)

(73) Assignee: Suphachatawong Innovation (TH)

( * ) Notice: Subject to any disclaimer, the term of this patent is extended or adjusted under 35 U.S.C. 154(b) by 34 days.

(21) Appl. No.: 13/815,825

(22) Filed: Mar. 15, 2013

(65) Prior Publication Data

US 2014/0283262 P1 Sep. 18, 2014

(51) Int. Cl.
*A01H 5/00* (2006.01)

(52) U.S. Cl.
USPC ..... Plt./311

(58) Field of Classification Search
USPC ..... Plt./311
See application file for complete search history.

*Primary Examiner* — Kent L Bell

(74) *Attorney, Agent, or Firm* — Cassandra Bright

(57) ABSTRACT

A new and distinct *Phalaenopsis* cultivar named 'SUPHAL1305' is disclosed, characterized by purple petals and sepals with white edges and netting as well as purple lip color and small green leaves. The new variety is a *Phalaenopsis*, typically produced as an indoor ornamental plant.

2 Drawing Sheets

Figure 1:
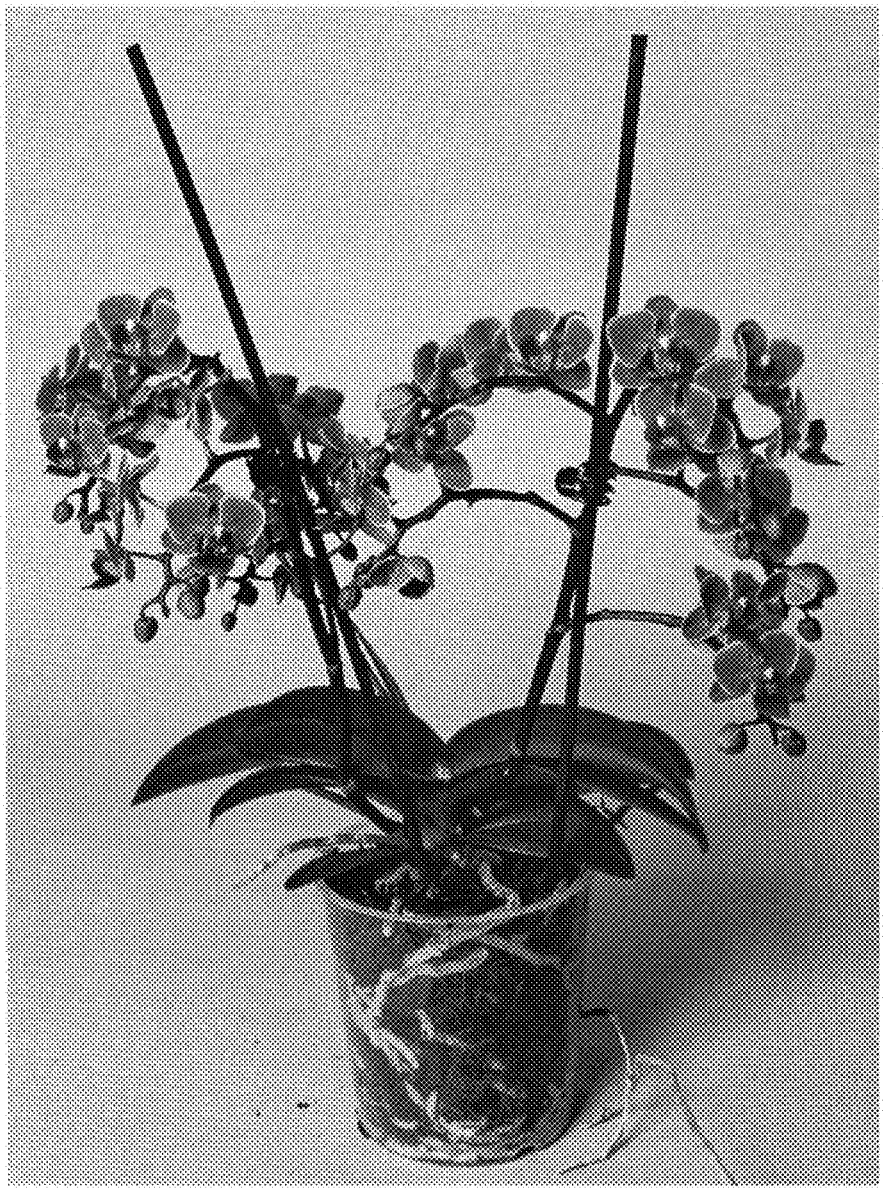

Latin name of the genus and species: *Phalaenopsis* hybrid.
Variety denomination: 'SUPHAL1305'.

BACKGROUND OF THE INVENTION

This application relates to a new cultivar of *Phalaenopsis* hybrid. The new variety is the product of a planned breeding program. The new variety originated as a seedling from the crossing of the unpatented, proprietary seed parent *Phalaenopsis* 'R1AMAS7' with the unpatented, proprietary pollen parent referred to as *Phalaenopsis* 'AD2S7'. The crossing was made by the inventor in his research greenhouse in Chonburi, Thailand in September of 2005.

The new variety was first selected by the inventor, Thumrong Suphachadiwong, a citizen of Thailand, in August of 2008 in a research greenhouse belonging to the inventor in Chonburi, Thailand. After identifying the new variety as a potentially interesting selection, the inventor continued confidential testing and propagation of 'SUPHAL1305', assessing stability of the unique characteristics of this variety.

Asexual reproduction of the new cultivar 'SUPHAL1305' was first performed at a commercial laboratory belonging to the inventor in Chonburi, Thailand by tissue culture in April of 2009. Access to all plants was restricted, as plants were kept in a greenhouse not open to the public, and tissue culture plantlets were in a laboratory belonging to the inventor, and not accessible to the public. Through subsequent propagation, multiple generations have been reproduced, which have shown that the unique features of this cultivar are stable and reproduced true to type.

SUMMARY OF THE INVENTION

The cultivar 'SUPHAL1305' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SUPHAL1305'. These characteristics in combination distinguish 'SUPHAL1305' as a new and distinct *Phalaenopsis* cultivar:

1. Purple petals and sepals with white edges and netting.
2. Small green leaves.
3. Purple lip color.

PARENT COMPARISON

Plants of the new cultivar 'SUPHAL1305' are similar to the seed parent, *Phalaenopsis* 'R1AMAS7' in most horticultural characteristics. The new variety, however, produces a more compact plant than the seed parent. Additionally the new variety produces smaller flowers of lighter color than the seed parent.

Plants of the new cultivar 'SUPHAL1305' are similar to the pollen parent, *Phalaenopsis* 'AD2S7' in most horticultural characteristics. Plants of the new variety however, produce flowers of different coloration than the pollen parent.

COMMERCIAL COMPARISON

'SUPHAL1305' is similar to the unpatented commercial variety *Phalaenopsis* 'Sogo F2526' in most horticultural characteristics. However the new variety, 'SUPHAL1305' differs from 'Sogo F2526' in the following characteristics:

1. Different lip and petal shape.
2. Petals are more widely spaced.
3. Purple apical lobe compared to red-purple of the comparator.
4. Smaller flower size.
5. Shorter plant height.
6. Leaves are darker green and glossier.

'SUPHAL1305' is similar to the unpatented commercial variety *Phalaenopsis* 'Sogo F1924' in most horticultural characteristics. However the new variety, 'SUPHAL1305' differs from 'Sogo F1924' in the following characteristics:

1. Different lip and petal shape.
2. Petals are further apart.
3. Smaller flower size.
4. Leaves are darker green and glossier.

BRIEF DESCRIPTION OF THE PHOTOGRAPH

The accompanying photographs in FIG. 1 illustrates in full color a typical plant of 'SUPHAL1305' grown in a commercial greenhouse in Zuidbroek, the Netherlands. This plant is approximately 18 months old after deflasking, shown planted in an 11 cm container.

Figure 2:
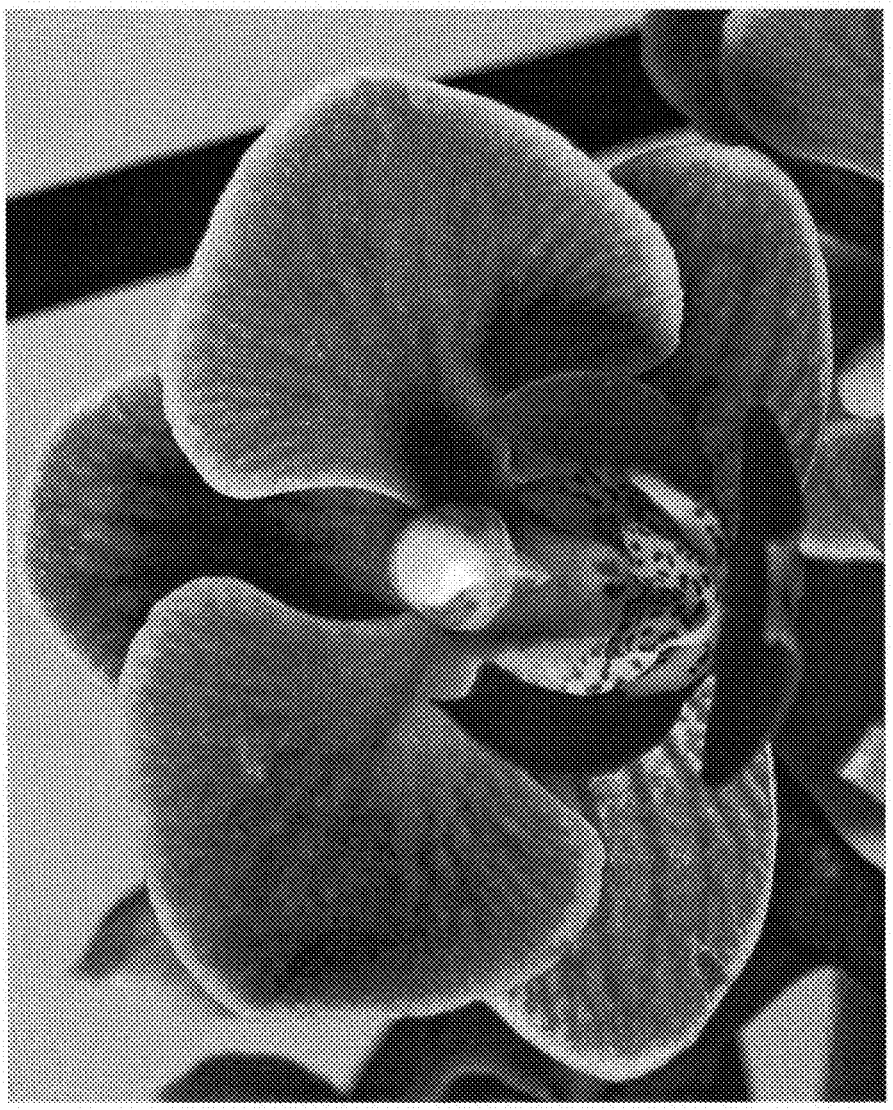

FIG. 2 illustrates a close up of the individual flower.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'SUPHAL1305' plants grown in a greenhouse in Zuidbroek, the Netherlands. This plant is approximately 18 months old after deflasking, shown planted in an 11 cm container. Temperatures ranged between 18° C. and 28° C. day and night. No photoperiodic or chemical treatments were given to the plants. During bright Summer conditions, shade was given. During dark Winter months, supplemental light was given at unspecified amounts. Measurements and numerical values represent averages of typical plant types.

Botanical classification: *Phalaenopsis* hybrid 'SUPHAL1305'.

PROPAGATION

Type of propagation typically used: Tissue culture.

Time to initiate roots: About 21 days at approximately 28° C.

Time to produce a rooted cutting/liner: About 26 weeks at approximately 18° C. to 28° C.

Root description: Thick (typical for *Phalaenopsis*) and rounded, average diameter: 5 mm, colored greyed-green; near RHS 194C.

PLANT

Growth habit: Monopodial.

Height from top of soil line to top of foliage: Average 7.6 cm.

Height from top of soil line to top of flowers: Average 22.5 cm.

Plant spread: At widest, average: 29.2 cm; at narrowest: 24.0 cm.

Normal pot size: 11 cm.

Growth rate: Moderate.

Number of leaves per plant: Average 12.

FOLIAGE

Leaf:

*Arrangement*.—Distichous.

*Average length*.—Approximately 11.7 cm (including sheath).

*Average width*.—Approximately 5.8 cm.

*Shape of blade*.—Elliptic.

*Aspect*.—Horizontal, slightly curled downward.

*Apex*.—Unequal acute, curled downward.

*Base*.—Cuneate. Sheath length: Average 1.1 cm. Sheath width: Average 0.9 cm. Sheath color: Green; near RHS 143B.

*Margin*.—Entire.

*Texture of top surface*.—Smooth, slightly furrowed.

*Texture of bottom surface*.—Smooth.

*Appearance of top surface*.—Glossy.

*Appearance of bottom surface*.—Moderately glossy.

*Color*.—Young foliage upper side: Green to yellow-green; near in between RHS N137A and 146A but darker. Young foliage under side: Yellow-green; near RHS 146A. Mature foliage upper side: Green; near RHS N137A. Mature foliage under side: Yellow-green; near RHS 146A.

*Venation*.—Type: Camptodromous. Venation coloration: Upper side green; near RHS N137A, under side yellow-green; near RHS 146A, main vein on under side green; near RHS 143A.

Petiole: No petiole present.

FLOWERING CHARACTERISTICS

Flower bud:

*Rate of opening*.—Approximately ten days after stage described. Length: Approximately 1.0 cm. Diameter: Approximately 0.8 cm wide and 1.0 cm high. Shape: Broad ovate. Color: Purple; near RHS N77D.

Peduncle:

*Length*.—Approximately 28.5 cm.

*Width*.—Approximately 0.5 cm.

*Aspect*.—Approximately 70° angle to rosette.

*Strength*.—Strong.

*Texture*.—Smooth.

*Appearance*.—Very slightly glossy.

*Color*.—Brown; near RHS 200A, heavily dotted yellow-green; near RHS 145A.

Inflorescence:

*Flowers per stem*.—Average 40.

*Inflorescence arrangement*.—Compound panicle.

*Inflorescence height*.—Approximately 12.9 cm (measured from lowest branching of panicle to top of inflorescence).

*Inflorescence width*.—Approximately 14.8 cm.

Individual flowers:

*Flower type*.—Single zygomorphic flower.

*Shape*.—Rounded deltate.

*Length* (*height*).—Approximately 3.2 cm.

*Width*.—Approximately 3.3 cm.

*Depth*.—Approximately 2.1 cm.

*Fragrance*.—No fragrance.

*Persistent*.—Non-persistent.

*Quantity of petals*.—2 true petals.

Petals:

*Arrangement*.—One petal on each side of the column.
*Length*.—Approximately 1.5 cm.
*Width*.—Approximately 1.85 cm.
*Shape*.—Deltoid.
*Apex*.—Obtuse to broad acute.
*Base*.—Cuneate.
*Margin*.—Entire.
*Texture*.—Upper (forward) surface: Smooth, velvety.
*Texture*.—Lower (back) surface: Smooth, velvety.
*Appearance*.—Matte, all surfaces.
*Color*.—When opening, forward surface: Purple-violet; near RHS N81B, purple towards the margins; near RHS 77B, outer margins white; near RHS NN155D. When opening, back surface: Purple to violet; a color between RHS 75B and 84B, margins white; near RHS NN155D. Fully Opened, forward surface: Purple-violet; near RHS N81B, purple towards the margins; near RHS 77B, outer margins white; near RHS NN155D. Fully Opened, back surface: Purple to violet; a color between RHS 75B and 84B, margins white; near RHS NN155D. Fading, forward surface: Not fading, only becoming non-velvety. Fading, back surface: Not fading, only becoming non-velvety.
*Color venation*.—Fully Opened, forward surface: Purple; near RHS N78A. Fully Opened, back surface: Purple; near RHS N78B, only main vein well visible.

Labellum:

*Shape*.—Three-parted.
*Length*.—Approximately 1.8 cm.
*Width*.—Approximately 1.6 cm.
*Texture*.—Smooth, dull, velvety.
*Appearance*.—Matte.
*Tip*.—Broad emarginated.
*Base*.—Cuneate.
*Color*.—When opening, forward surface: Central lobe purple; near RHS N79C, slightly tinged red-purple; near RHS 59A, purple-violet towards the top; N80A. Lateral lobes purple; near RHS N79B and N79C, base white; near RHS NN155C, tinged yellow; near RHS 7C and 7D, dotted purple; near RHS N79B callosities yellow; near RHS 12A, dotted purple; near RHS N79C. When opening, back surface: Central lobe purple-violet; near RHS N80A, slightly more purple at the base; near RHS N79C, central part purple; 76A, lateral lobes purple; near RHS N79B and N79C, base white; near RHS NN155A. Fully Opened, forward surface: Central lobe purple; near RHS N79C, slightly tinged more red-purple; near RHS 59A, purple-violet towards the top; N80A, lateral lobes purple; near RHS N79B and N79C, base white; near RHS NN155C, tinged yellow; near RHS 7C to 7D, dotted purple; near RHS N79B callosities yellow; near RHS 12A, dotted purple; near RHS N79C. Fully Opened, back surface: Central lobe purple-violet; near RHS N80A, slightly more purple at the base; near RHS N79C, central part purple; 76A, lateral lobes purple; near RHS N79B to N79C, base white; near RHS NN155A. Fading, forward surface: Not fading, only becoming non-velvety. Fading, back surface: Not fading, only becoming non-velvety.
*Color venation*.—Fully Opened, forward surface: No venation visible. Fully Opened, back surface: No venation visible. Margin: Entire.

Sepals:

*Quantity*.—3.
*Appearance*.—Matte.
*Length*.—Approximately 1.6 cm.
*Width*.—Dorsal sepal approximately 1.5 cm. Lateral sepals approximately 1.4 cm.
*Shape*.—Ovate.
*Apex*.—Obtuse.
*Base*.—Broad cuneate.
*Margin*.—Entire.
*Texture*.—Smooth, velvety.
*Appearance*.—Matte.
*Color*.—Fully Opened, forward surface: Purple-violet; near RHS N81B, purple towards the margins; near RHS 77B, margins white; near RHS NN155D, veined purple; near RHS N78A, lateral sepals with a small purple spot at the base; near RHS 76D. Fully Opened, back surface: Purple to violet; near in between RHS 75B and 84B, margins white; near RHS NN155D, veined purple; near RHS N78B.

Pedicels:

*Length*.—Approximately 1.6 cm.
*Diameter*.—Approximately 0.15 cm.
*Angle*.—Approximately 85° to peduncle.
*Strength*.—Moderately strong.
*Texture*.—Smooth.
*Appearance*.—Moderately glossy.
*Color*.—Greyed-red; near RHS 182C and 182D.

REPRODUCTIVE ORGANS

*Stamens, style and stigma fused into column*?.—Yes.
*Column length*.—Approximately 0.8 cm.
*Column diameter*.—Approximately 0.4 cm.
*Column color*.—Purple-violet; near RHS N80A.
*Ovary*.—Position: Inferior. Diameter: Approximately 0.3 cm. Color: Purple-violet; near RHS N80B.
*Pollen color*.—Yellow-orange; near RHS 21A.

OTHER CHARACTERISTICS

Disease resistance: Neither resistance nor susceptibility to the normal diseases found in *Phalaenopsis* has been observed.
Drought tolerance and cold tolerance: Normal for species.
Fruit/seed production: No fruits/seeds detected to date.

What is claimed is:

1. A new and distinct cultivar of *Phalaenopsis* plant named 'SUPHAL1305' as herein illustrated and described.

* * * * *